United States Patent [19]

Lingenhöle et al.

[11] 4,278,427
[45] Jul. 14, 1981

[54] COMPRESSED-AIR DENTAL MOTOR

[75] Inventors: Bernhard Lingenhöle, Biberach; Ernst Strohmaier, Bad Schussenried, both of Fed. Rep. of Germany

[73] Assignee: Kaltenbach & Voight GmbH & Co., Fed. Rep. of Germany

[21] Appl. No.: 73,294

[22] Filed: Sep. 7, 1979

[30] Foreign Application Priority Data

Sep. 12, 1978 [DE] Fed. Rep. of Germany ....... 2839632

[51] Int. Cl.³ .............................................. A61C 1/02
[52] U.S. Cl. ..................................... 433/100; 415/36; 91/59; 173/12
[58] Field of Search .................. 433/100, 132, 99, 98, 433/28; 415/36, 38, 503; 91/59; 173/12

[56] References Cited

U.S. PATENT DOCUMENTS

| | | | |
|---|---|---|---|
| 2,570,009 | 10/1951 | Schmid | 433/100 |
| 2,725,918 | 12/1955 | Deshler | 91/59 |
| 2,899,941 | 8/1959 | Adams | 91/59 |
| 3,049,098 | 8/1962 | Inoue | 91/59 |
| 3,162,250 | 12/1964 | Sindelar | 91/59 |
| 3,253,662 | 5/1966 | Sacchini | 173/12 |
| 3,442,177 | 5/1969 | Ulbing et al. | 415/36 |
| 3,461,975 | 8/1969 | Ulbing | 91/59 |
| 3,472,323 | 10/1969 | Hall | 415/503 |
| 3,477,793 | 11/1969 | Kitagawa | 415/36 |
| 3,578,872 | 5/1971 | McBurnie | 433/132 |

*Primary Examiner*—Gene Mancene
*Assistant Examiner*—John J. Wilson
*Attorney, Agent, or Firm*—Scully, Scott, Murphy & Presser

[57] ABSTRACT

A compressed-air dental motor includes a housing, a rotor, a compressed air inlet conduit supplying compressed air for placing the rotor into rotation, and a rotor shaft in the rotor connectable with a work tool, such as a drill. A valve member in the housing associated with the compressed-air inlet conduit is adapted to vary the inlet of compressed air for each unit of time, and an adjusting device is provided for controlling the valve member. The rotor shaft includes an axially displaceable component for controlling the valve member in direct mechanical dependence upon the torque at the work tool so as to form the adjusting device into a torque-dependent adjusting device.

5 Claims, 7 Drawing Figures

COMPRESSED-AIR DENTAL MOTOR

BACKGROUND OF THE INVENTION

1. Field of the Invention

The present invention relates to a compressed-air dental motor, consisting of a housing having a rotatably supported rotor arranged therein adapted to be set into rotation through compressed air introduced into the housing through the intermediary of a compressed-air inlet conduit; which includes a rotor shaft connectable with a tool, for instance a drill, wherein the compressed-air inlet conduit is associated with a valve arrangement located in the housing which is adapted to vary the compressed air infeed for each unit of time and which is controllable by means of a setting mechanism.

2. Discussion of the Prior Art

The compressed-air motor, for example, may in accordance with German laid-open patent application No. 19 41 159 be constructed as a turbine which has a rotor provided with blades; or pursuant to German published patent application No. 12 32 789 as a piston motor having a rotor provided with cylinders for pistons, for instance in the form of balls; or pursuant to German laid-open patent application No. 23 04 666 as a vane motor having a rotor which is provided with slits for receiving radially movable vanes.

In the compressed-air motor which has become known from German laid-open patent application No. 19 41 159, which is constructed as a turbine with a rotor equipped with blades wherein the compressed-air motor is only similar to the above-mentioned types. The setting mechanism consists of an electrical inductance coil located within the motor housing, in which there are induced voltage shocks through permanent magnets which are inserted in the rotor. At the loading of the work tool, the rotational speed of the rotor will reduce. This reduction in the rotational speed is transmitted through the inductance coil to a switch box arranged externally of the motor which includes an electrical control circuit, in the form of electrical amplitudes, and which emits an actuating amplitude, so as to be able to control in an electromagnetic manner the valve arrangement which is located within the compressed-air inlet conduit, also similarly arranged externally of the motor, for the purpose of varying the compressed air inlet to the motor for each unit of time. The arrangement, especially the switch box externally of the motor, demands special spatial requirements. Moreover, this known compressed air motor can only be employed in locations in which there is available an electrical connection.

In the compressed-air motor of the above-mentioned type which has become known through German published patent application No. 12 32 789, which is constructed as a piston motor with cylinders for pistons which, for example, are shaped as spheres, and, in a space-saving manner with the valve arrangement being located within the housing, the rated speed of the motor is presettable by varying the cross-section of the outlet aperture of the exhaust air, in effect, without necessity for an electrical connection. The exhaust air conduit includes a branch conduit which leads to a diaphragm chamber possessing a diaphragm which forms the adjusting arrangement, wherein the diaphragm exerts an effect on a slide valve which forms the valve arrangement. The adjusting arrangement which is constructed in this manner has the function thereof dependent upon the set cross-section of the exhaust air outlet aperture and, consequently serves only for the stabilizing of the rated speed of the motor. Particularly at a lower set rated speed, due to dependence upon the cross-section of the exhaust air outlet aperture it is not possible to obtain an increase in the torque at the loading of the work tool, since the therefore required additional compressed-air quantity to be introduced for each unit of time after passage through the displacement volume of the motor cannot pass as exhaust air through the mentioned cross-section of the exhaust air outlet aperture, thus possibly leading to the stalling of the motor. For the remainder, this known arrangement can only be employed with closed, or effectively, sealingly constructed types of air motors, but not with openly constructed compressed-air motors, such as are represented by vane motors, in which the rotor is set into rotation through "relaxing."

The vane motor which has become known through German laid-open patent application No. 23 04 666 does not at all include a valve arrangement which is controllable through a setting arrangement for varying the compressed air infeed for each unit of time, as a result of which this motor, which belongs to an entirely different class of construction, will stall upon the loading of the work tool.

The present invention thus proceeds as an improvement over the compressed-air motor which has become known from Germain laid-open patent application No. 12 32 789.

SUMMARY OF THE INVENTION

Accordingly, an object of the present invention is to provide a compressed-air dental motor of the above-mentioned type in which, while retaining the avoidance of a particular spatial requirement and a spatial electrical connection, ensures an increase in the torque put out by the motor dependent upon the magnitude of an occurring loading of the work tool, for example, a drill, so as to avoid, for instance, the stalling of the drill in the tooth during the drilling out of dental cavities, which would be uncomfortable to the patient, and particularly also for compressed-air motors which are constructed as vane motors.

The advantages attained through the present invention can be essentially ascertained in that the axially slideable component serving for the control of the valve arrangement, independently of the cross-section of the exhaust air outlet aperture, is caused to be directly axially displaced by the loaded work tool for the purpose of controlling the valve arrangement, so that the proposed construction is also suitable for compressed-air motor types which are not closed, such as vane motors. Due to the independence from the size of the cross-section of the exhaust air outlet aperture, even at lower rated motor speeds is there achieved an effective increase in the torque. In this manner there is afforded that the compressed-air quantity introduced for each unit of time is automatically regulated to the torque demanded at the work tool, when there is required at the work tool a larger torque in the case of the loading thereof then that which is produced by the motor at its rated speed.

BRIEF DESCRIPTION OF THE DRAWINGS

In the drawings are illustrated exemplary embodiments of the invention; in which.

DETAILED DESCRIPTION

Figure 1:
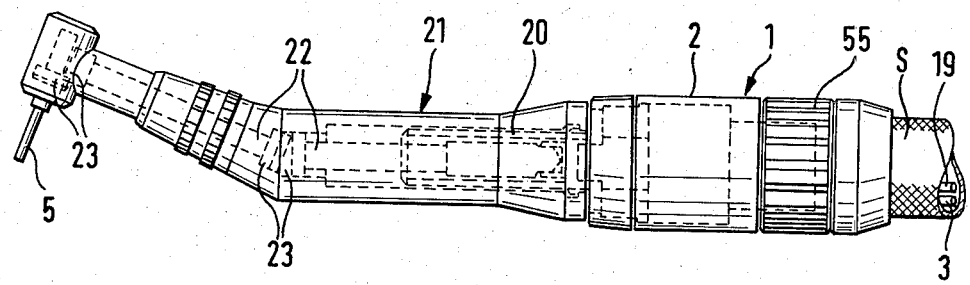
FIG. 1 is a plan view of a compressed-air dental motor with a mountable handpiece coupled thereto.

The compressed-air dental motor 1, which is constructed as a vane motor, consists of a sleeve-shaped housing 2 which forms the stator in which there is arranged a rotatably supported rotor 4 adapted to be set into rotation by means of compressed air introduced into the housing through a compressed-air inlet conduit 3; wherein the rotor includes a rotor shaft 6 connectable to a work tool 5, for example, a drill. The rotor 4 is supported within housing 1 in the endwise housing closures 7 and 8 by means of ball bearings 9, 10. The axis of rotation D of the rotor 4 extends in parallel relative to the axis A of the circular cylindrical inner wall 11 of an inner stationery housing insert 60 and is offset with respect to the latter.

Radially movably supported in longitudinal slits 12 of the rotor 4 are vanes 13 which have their outer ends 14 extend towards the circular cylindrical inner wall 11.

Openings 15, 16, and 17 communicate with the displacement chamber 18 of the motor 1 located between the rotor 4 and the circular cylindrical wall 11. As long as the opening 15 is subjected to compressed air and as a result acts as an air inlet aperture, the openings 16, 17 are air outlet apertures. When in contrast therewith, for the purpose of the subsequently explained change in the direction of rotation, the opening 16 is subjected to compressed air and as a result acts as an air inlet aperture, the openings 15, 17 become air outlet apertures. Thereby, the opening 17 always remains an air outlet aperture. Upon subjecting the motor 1 to compressed air, the last-mentioned enters through the air inlet aperture, for example opening 15, into the displacement chamber 18 and pushes the closest positioned vane 13 which is the furthest extended from the rotor 4, ahead thereof, so that the rotor 4 begins to rotate and the next vane 13 is subjected to the compressed air. The exhaust air escapes into the open through the air outlet apertures, for example openings 16, 17 through the exhaust air conduit 19 the last mentioned of which, such as the compressed-air inlet conduit 3, is arranged in a flexible supply hose S leading to the motor 1. The rotational speed of the vane motor may, for example, be approximately 20,000 to 100,000 r.p.m.

The motor 1, at the work tool-sided end thereof, includes an extension 20 for insertion into a receiving aperture of a dental handpiece 21 which is formed as an attachment. The handpiece 21 is in a known and therefore not illustrated manner, detachably connectable with the compressed-air motor 1. In the formation of this connection, a drive shaft 22 which arranged interiorly of the handpiece 21 also comes into engagement with the rotor shaft 6 of the motor 1. The drive shaft 22 sets the work tool 5 into rotation through the intermediary of a plurality of gears 23 or the like which are arranged at angles relative to each other.

The compressed-air inlet conduit 3 has a valve arrangement 24 associated therewith which varies the introduced compressed air quantity for each unit of time, which is located interiorly of the housing 2 and is controllable through an adjusting arrangement 25. The adjusting arrangement 25 is located intermediate the rotor 4 and the area of the rotor shaft 6 at the work tool end.

In order that the adjusting arrangement 25 torque-dependently responds to the loading of the work tool 5 extending above the normal loading, the rotor shaft 6 is provided with an axially displaceable component 26 which controls the valve arrangement 24 in direct mechanical dependence upon the torque taken off at the work tool, meaning, independently of the size of the cross-section of the exhaust air outlet. The axially displaceable component 26 is formed by a sliding sleeve non-rotatably mounted on the rotor shaft 6 and, butting surfaces or approach cam tracks 27 in a type of spiral toothing which for carrying out of the axial movement of the component 26, cooperate with just such counter butting surfaces or approach cam tracks 28 of a component 29 mounted axially nondisplaceably and with limited rotation on the rotor shaft 6, so as to further transmit the rotational movement of the rotor shaft 6 to the work tool 5. When now the work tool 5 is more extensively loaded, then the component 29 is hereby braked or restrained, whereas the component 26 is continued to be driven by the rotor shaft 6. This has as a result that the butting surfaces or approach cam tracks 27, 28 slide along each other in a manner whereby the component 26 is axially displaced in the sense of a withdrawal from the component 29 and hereby controls the valve arrangement 24 for the purpose of increasing the introduced air quantity for each unit of time.

In order to achieve the non-rotatability and concurrently the axial displaceability, the component 26 possesses at least one, and preferably two diametrically oppositely located axial slits 30 in which there engage radial pins 31 fixedly arranged on the rotor shaft 6. The axial slits 30 extend from one end of the component 26 which is formed as a sliding sleeve, whereas at the other end, namely at the end proximate the work tool, there are arranged the butting surfaces or approach cam tracks 27. The component 26 has additionally associated therewith a spring 32 for effecting the assumption of the engaged position of its butting surfaces or approach cam tracks 26 with the counter butting surfaces or approach cam tracks 28 of the limitedly rotatable component 29.

The limitedly rotatable, axially undisplaceable component 29 is formed by a rotatable sleeve which is supported on the rotor shaft 6 which includes a radial slit 33 correlated in its length with the length of the axial movement of the axially displaceable component 26, and in which there engages a radial pin 34 fixedly mounted on the rotor shaft 6. There now occurs an increased loading on the work tool 5, then the components 26 and 28 rotate relatively to each other until the radial pin 34 comes into contact at the end of the radial slit 32. During this displacement the butting surfaces or approach cam tracks 27, 28 slide off each other so that the component 26 withdraws from the component 29 and thereby the valve arrangement 24 controls in the sense of an increase in the introduced air quantity per unit of time.

Figure 3:
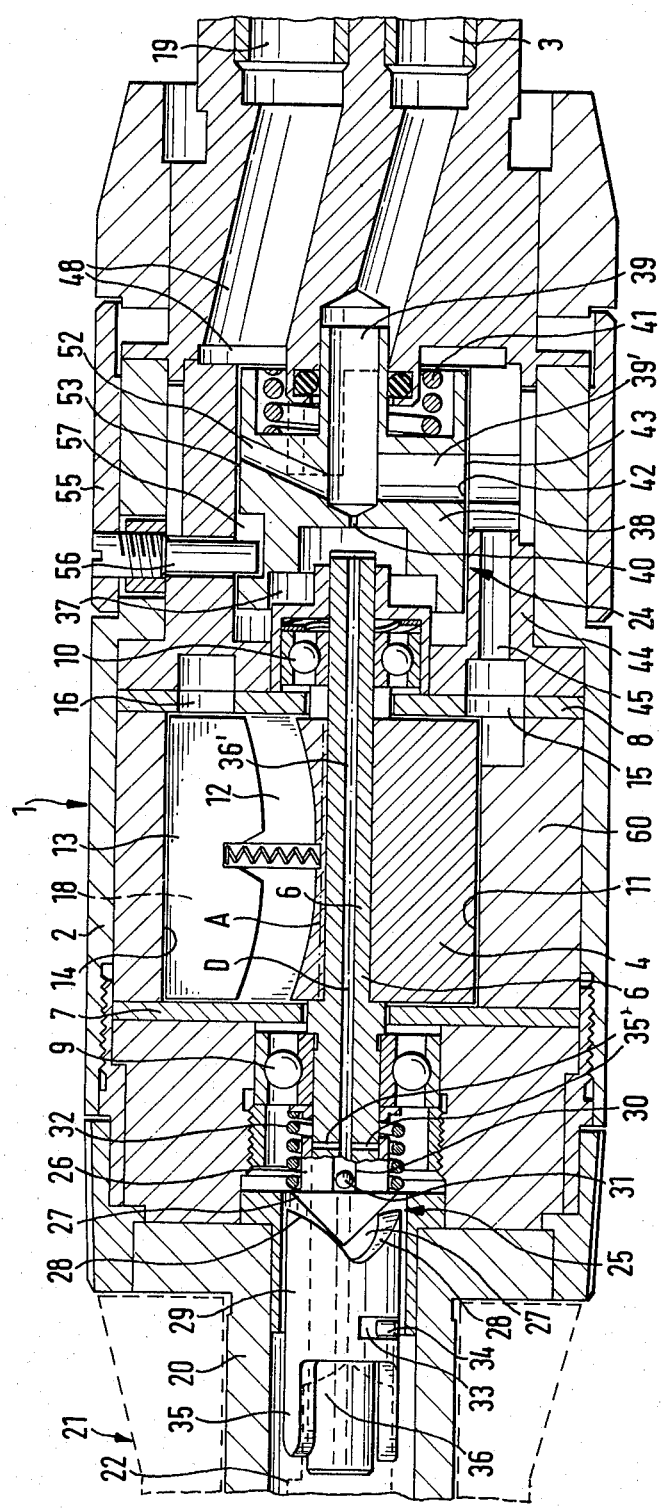
FIG. 3 is a sectional view through the compressed-air motor at a loaded work tool.
Figure 3:
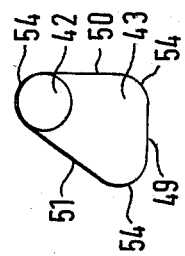

For the continued transmission of the rotational movement of the rotor shaft 6 obtained through the motor 1 to the work tool 5, the component 29 which is formed by the rotatable sleeve, which is limitedly rotatable with respect to the rotor shaft 6 but axially non-slidable, is provided with follower elements 35 which, pursuant to FIG. 3, are in engagement with follower element 36 on the drive shaft 22 of the handpiece 21.

As may be ascertained from FIG. 3, on the ends facing each other of the sliding sleeve-forming component 26 as well as on the butting surfaces or approach cam tracks 27, 28 of the rotatable sleeve forming the component 29, are presently constructed in the type of the teeth of a spur gear.

Figure 2:
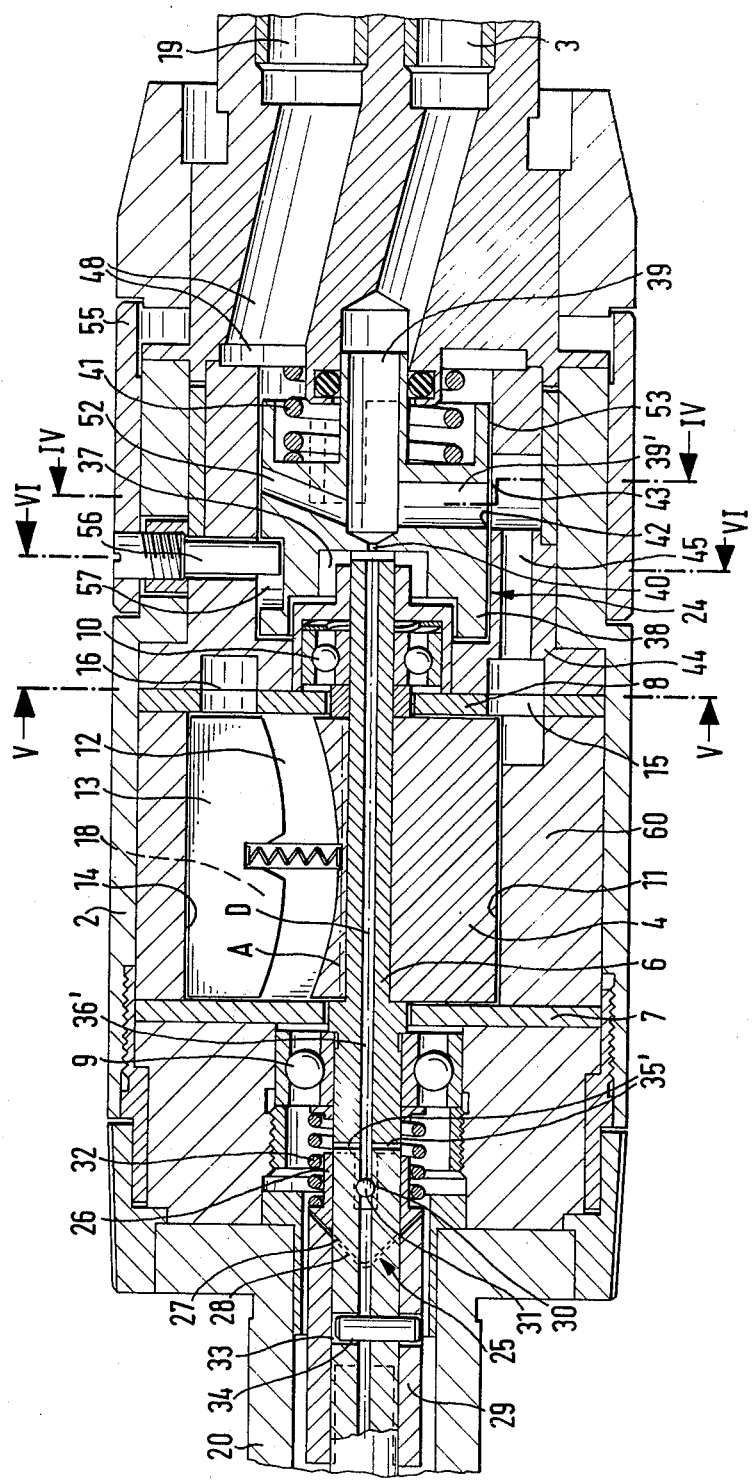
FIG. 2 is an enlarged longitudinal sectional view through the compressed-air motor at a normal or an unloaded work tool.
Figure 2:
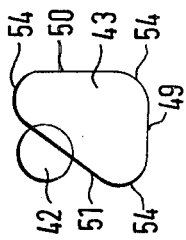

The rotor shaft 6 is provided with a control air channel 36' extending from the end remote from the work tool into the axially displaceable component 26 in its engaged position with the axially non-displaceable component 29 covered region of the rotor shaft 6, and which includes therein at least one radial outlet passageway 35'. Hereby the mouths of the two outlet passageways 35' provided pursuant to FIGS. 2 and 3, are in the mentioned engaged position coverable by the axially non-slidable component 29 for the purpose of venting the control air into the open end, in the disengaged position, for the purpose of actuating the vavle arrangement 24. At the end towards the work tool, the control air passageway 36' is closed off by the radial pin 31 which engages into the axial slit 30 in the sliding sleeve.

At the end of the rotor shaft 6 remote from the work tool, the control air passageway 36' terminates in a displacement chamber 37 of an axially movably supported piston-like valve member 38 which forms the valve arrangement 34, which includes a compressed-air passageway 39 constantly connected with the compressed-air inlet conduit 3 of the motor 1, and which leads to the displacement chamber 18 of the motor 1, which includes a branch passageway 40 subjected to compressed air, which at the freeing of the mouth of the one or the radial passageways 35' is connected with the mouth of the control passageway 36' directed into the displacement chamber 37 and, upon the covering of the mouth of the or mouths the radial outlet passageways 35' of the referred to displacement chamber 37, for effecting an axial movement of the piston-like valve member 38 for increasing the compressed air inlet to the displacement chamber 18 of the motor 1 for each unit of time. Achieved in this manner, in a particularly simple way is an increase in the torque. In order that upon the ending of the overloading of the work tool 4 the branch passageway 40 again comes into communication with the mouth of the control air passageway 36', a return spring 41 is associated with the piston-like valve member 38.

Figure 4:
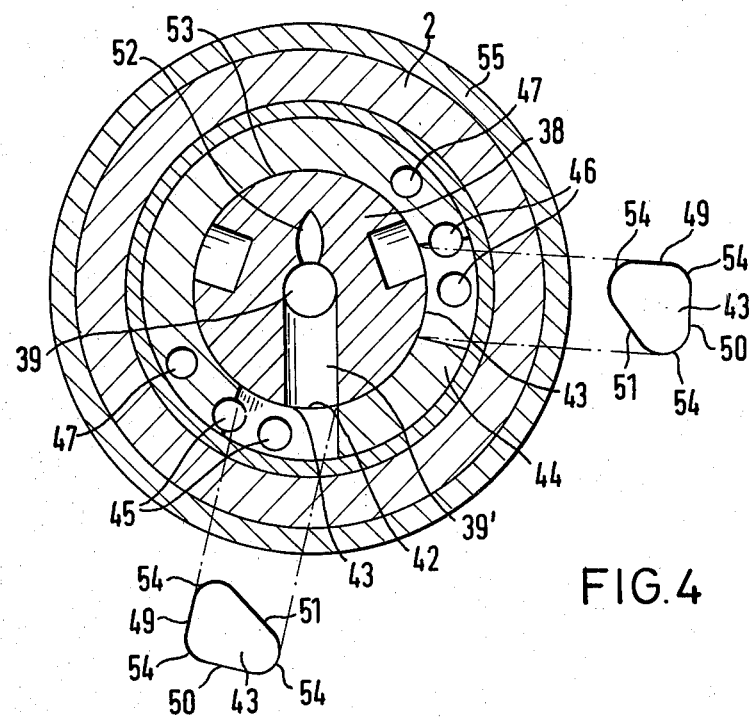
FIG. 4 is a section taken along line IV—IV in FIG. 2.
Figure 5:
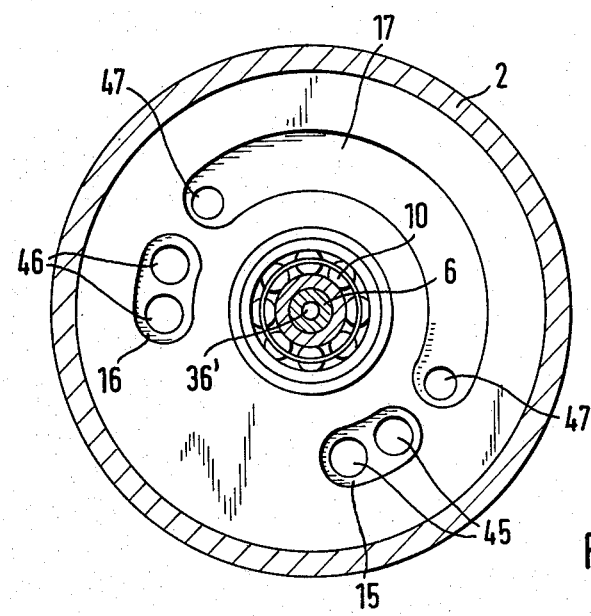
FIG. 5 is a section taken along line V—V in FIG. 2.

The compressed-air inlet passageway 39 of the piston-like valve member 38 is constantly in communication, through the intermediary of a radial inlet aperture 42 of a connecting bore 39' having a larger cross-section as the last occupied radial inlet aperture 43 of two continuing passageways 45, 46 leading over the opening 15 or 16 to the displacement chamber 18 of the motor 1, and which are arranged in a stationary housing portion 44. Hereby, the mentioned inlet aperture 43, pursuant the stroke position of the piston-like valve member 38 at release of the mouth of or mouths of the radial outlet passageways 35' is adapted to be covered less and upon the covering of the mentioned mouths more with the radial outlet aperture 42 of the compressed-air inlet passageway 39. The exhaust passageways which lead from the air exhaust aperture 17 to the exhaust air conduit 19 are designated with reference numerals 47 and 48. From FIGS. 2 and 3, in combination with FIG. 4, there may be ascertained that the piston-like valve member 38 is circularly constructed in cross-section and supported so as to be limitedly rotatably in the stationary housing portion 44, whereby the radial inlet aperture 43 of the continuing passageway 45, 46 is essentially triangular and includes an axial boundary edge 49 as well as a radial boundary edge 50 extending therefrom. The boundary edges 49, 50 subtend a right angle with each other. The other ends of the boundary edges 49, 50 are connected with each other through an inclined extending boundary edge 51, like a type of screwline. Met hereby is such an arrangement in which the length of the axial boundary edge 49 is correlated with the axial path of movement of the piston-like valve member 38, and the length of the radial boundary edge 50 with the radial path of rotation of the piston-like valve member 38, with the task that upon release of the mouth of or mouths of the radial outlet passageways 35', in the one rotational position of the piston-like valve member 38 corresponding to a low rated motor speed, only a small covering or superposition of the outlet opening 42 is effected with the inlet opening 43, whereas in another rotational position of the piston-like valve member 38 corresponding to a higher rated motor speed, the outlet opening 42 is fully located within the cross-section of the inlet opening 43 and, namely, under contacting of the edge of the outlet opening 42 against the axial boundary edge 49 of the inlet opening 43.

The axial and the rotational movement of the piston-like valve member 38 is rendered easier in that a radial passageway 52 branches off from its pressure inlet passageway 39, outwardly terminating for subjecting the annular gap 53 located between the stationary housing portion 44 possessing the circularly cylindrical inner surface and the circularly cylindrical outer wall of the valve member 38 with compressed air. Produced hereby is an air bearing, since an air film will build up in the annular gap 53.

A particularly good correlation with the rated motor is obtained particularly when the last-mentioned is relatively low, when the corners 54 of the essentially triangular inlet aperture 43 are rounded off, and the radius of the rounded off portions corresponds to the radius of an outlet aperture 42 for the compressed-air inlet passageway 39 of the piston-shaped valve member 38, which has a circular cross-section.

Figure 6:
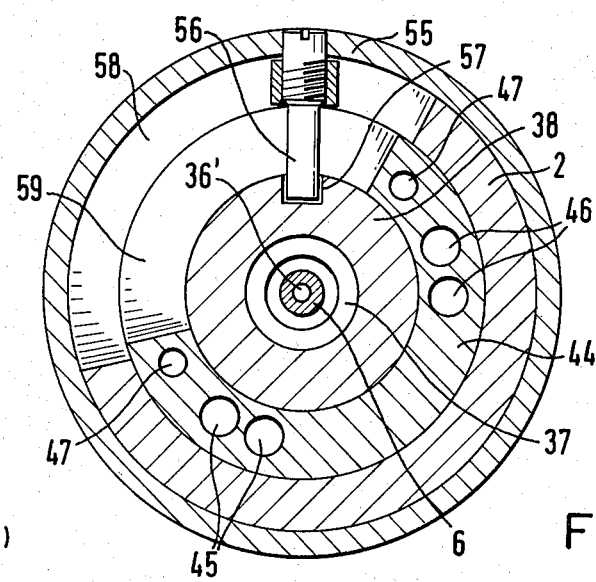
FIG. 6 is a section taken along line VI—VI in FIG. 2.
Figure 7:
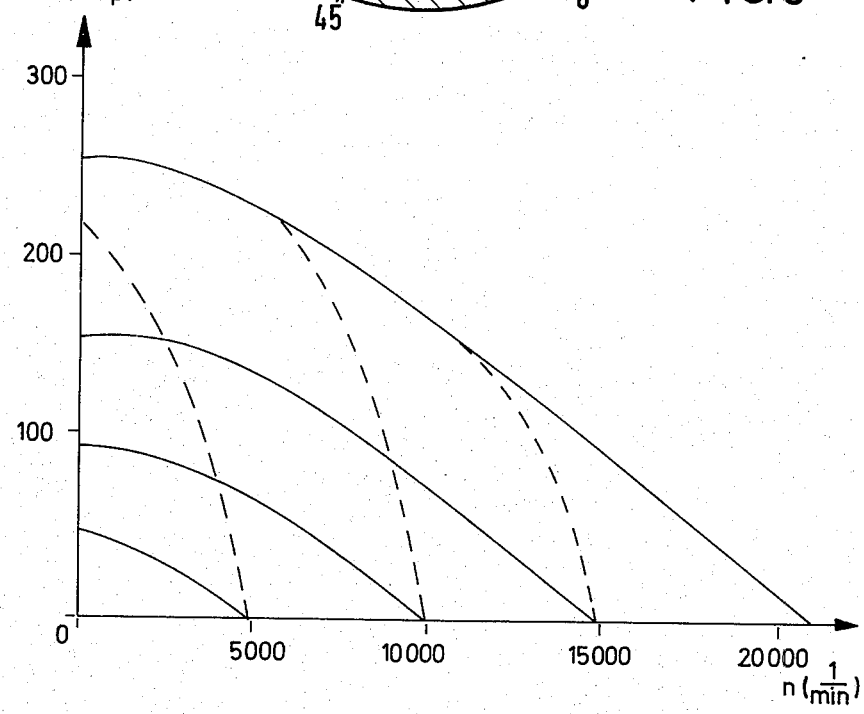
FIG. 7 is a graph of the torque obtainable at different rated motor speeds without increase in the compressed air infeed, meaning, at an unloaded work tool in the solid lines, and with an increase in the compressed-air infeed, in effect with a loaded work tool shown in dashed lines.

From FIGS. 2 and 3, in combination with FIG. 6, there may be ascertained that for a displacement of the piston-like valve member 38 to cause a change in the rated motor speed, on the outer wall of the housing 2 there is exteriorly rotatably mounted an adjusting ring 55 which is provided with a radial follower pin 56 traversing the housing 2 and the stationary housing portion 44, which engages in a radial recess 57 provided in the piston-like valve member 38 and which has an axial length corresponding to the axial stroke movement of the valve member 38. The housing 2 and the stationary housing portion 44 each include a cut out 58, 59 for the passing through of the follower pin 56, which extend over a radial length determining the rotational movement of the piston-like valve member 38.

For the easy effectuation of a change in the direction of rotation, provided in the wall of the essentially circularly cylindrical stationary housing portion 44 are two passageways 45, 46 arranged at a distance correlated with the right-hand and the left-hand rotation of the rotor, presently twice as close to each other, of which in accordance with the rotated position of the piston-like valve member 38, one serves selectively as a continuing passageway and the other as an exhaust air passageway.

The doubly provided passageways 47 which, independently of the rotational position of the piston-like valve member 38 constantly act as exhaust air passageways, are provided in addition to the passageways 45, 46 serving selectively as continuing passageway and as air exhaust passageway in the stationary housing portion 44.

What is claimed is:

1. A compressed-air dental motor comprising: a housing; a rotor; a compressed air inlet conduit supplying compressed-air for placing said rotor into rotation; a rotor shaft in said rotor connectable with a work tool, such as a drill; valve means in said housing associated with said compressed-air inlet conduit for varying the inlet of compressed air per unit of time; and adjusting means for controlling said valve means; the improvement comprising: said rotor shaft including an axially displaceable first component (26) arranged intermediate said rotor (4) and the end of said rotor shaft proximate the work tool (5) for controlling said valve means (24) in direct mechanical dependence upon the torque at said work tool (5) so as to form said adjusting means into a torque-dependent adjusting means, said axially displaceable component (26) including first contact surfaces or cam tracks (27), and a further component (29) arranged on said rotor shaft (6) for limited rotation but which is not axially displaceable including complementary contact surfaces or cam tracks (28) cooperating with said first contact surfaces or cam tracks to effect axial displacement of said first component (26) and to transmit the rotation of said rotor shaft (6) to said work tool (5); said rotor shaft having a control air passageway (36') extending from the end opposite said work tool to the region of said rotor shaft covered in the engaged position of said first component (26) and said further component (29); said control air passageway (36') including at least one radial outlet passageway (35') in said region whereby the outlet of said outlet passageway (35') in the engaged position is adapted to be covered by said first component (26) for venting the control air into the atmosphere and in the disengaged position of said components for actuating said valve means (24), said valve means comprising an axially movable piston-like valve member (38) having a displacement chamber (37), said control air passageway (36') communicating with said displacement chamber (37), said valve means (24) including a compressed air inlet conduit communicating with the work space of said motor and being constantly connected with a compressed-air inlet conduit of said motor; and a branch passageway (40) of said compressed-air inlet passageway for said valve member which is in communication with the control air passageway (36') when the outlet of said radial outlet passageway (35') is open, and when the opening of said radial passageway (35') is covered, compressed air from branch passageway (40) fills said displacement chamber (37) so as to effect an axial movement of said piston-like valve member (38) to increase the compressed air delivered to the work space of the motor per unit of time.

2. Compressed-air motor as claimed in claim 1, said valve member (38) being circular in cross-section and supported for limited rotation within a stationary housing portion (44), a radial inlet aperture (43) of a continuing passageway (45, 46) being substantially triangular and having an axial boundary edge (49) and a radial boundary edge (50) extending therefrom, an inclined boundary edge in the form of a screw-line (51) connecting said boundary edges, the length of said axial boundary edge (49) being correlated with the extent of axial movement of said valve member (38), and the length of the radial boundary edge (50) being correlated with the extent of radial rotation of said valve member (38), with the feature that at the opening of the outlet of said radial passageway (35') in one rotational position of said valve member, corresponding to a low motor rated rotational speed, only a small covering is effected between the outlet aperture (42) and the inlet aperture (43), whereas another rotational position of said valve member corresponds to a high motor rated rotational speed with the outlet aperture (42) fully located within the cross-section of the inlet aperture (43) and with contacting of the edge of the outlet aperture (42) against the axial boundary edge (49) of the inlet aperture (43).

3. Compressed-air motor as claimed in claim 2, comprising an adjustment ring (55) being rotatably supported on the outer wall of said housing (2) for rotation of said valve member (38) effecting a change in the rated motor speed, a radial follower pin (56) on said ring extending through said housing (2) and the stationary housing portion (44) and engaging in a radial recess (57) formed in said valve member (38), said follower pin (56) having a length corresponding to the axial stroke movement of said valve member (38), said housing (2) and said stationary housing portion (44) each having a recess (58, 59) for passing through of said follower pin (56) extending over a radial length conforming to the extent of rotation of said valve member (38).

4. Compressed-air motor as claimed in claim 2 or 3, comprising at least two passageways (45, 46) being formed in the wall of the essentially circularly cylindrical stationary housing portion (44) at a distance determined for the right-hand and left-hand rotation of said motor (1), each passageway serving in conformance with the rotational position of said valve member (38) selectively as either a continuing passageway and the other as an exhaust air passageway.

5. Compressed-air motor as claimed in claim 4, comprising at least one additional passageway (45, 46) constantly forming an exhaust air passageway independently of the rotated position of said valve member (38) being arranged in said stationary housing portion (44).

* * * * *